United States Patent [19]

Cragg et al.

[11] Patent Number: 5,782,861
[45] Date of Patent: Jul. 21, 1998

[54] PERCUTANEOUS HEMOSTASIS DEVICE

[75] Inventors: Andrew H. Cragg, Edina, Minn.; Rodney Brenneman, Dana Point, Calif.

[73] Assignee: Sub Q Inc.

[21] Appl. No.: 778,045

[22] Filed: Dec. 23, 1996

[51] Int. Cl.$^6$ .................. A61B 17/08; A61D 1/00
[52] U.S. Cl. .................. 606/216; 606/215; 606/219
[58] Field of Search .................. 606/213, 215, 606/216, 217, 219, 220, 221

[56] References Cited

U.S. PATENT DOCUMENTS

| | | | |
|---|---|---|---|
| 4,619,261 | 10/1986 | Guerriero | 128/325 |
| 4,852,568 | 8/1989 | Kensey | 128/325 |
| 4,890,612 | 1/1990 | Kensey | 606/213 |
| 4,929,246 | 5/1990 | Sinofsky | 606/8 |
| 5,021,059 | 6/1991 | Kensey et al. | 606/213 |
| 5,061,274 | 10/1991 | Kensey | 606/213 |
| 5,221,259 | 6/1993 | Weldon et al. | 604/96 |
| 5,222,974 | 6/1993 | Kensey et al. | 606/213 |
| 5,234,447 | 8/1993 | Kaster et al. | 606/213 |
| 5,275,616 | 1/1994 | Fowler | 606/213 |
| 5,342,388 | 8/1994 | Toller | 606/201 |
| 5,342,393 | 8/1994 | Stack | 606/213 |
| 5,383,899 | 1/1995 | Hammerslag | 606/214 |
| 5,391,183 | 2/1995 | Janzen et al. | 606/213 |
| 5,403,333 | 4/1995 | Kaster et al. | 606/219 X |
| 5,417,699 | 5/1995 | Klein et al. | 606/144 |
| 5,419,765 | 5/1995 | Weldon et al. | 604/96 |
| 5,478,353 | 12/1995 | Yoon | 606/216 X |
| 5,486,195 | 1/1996 | Myers et al. | 606/213 |
| 5,527,322 | 6/1996 | Klein et al. | 606/144 |

FOREIGN PATENT DOCUMENTS

95/32671  7/1995  WIPO.

*Primary Examiner*—Sam Rimell
*Assistant Examiner*—Luke Yeh
*Attorney, Agent, or Firm*—Klein & Szekeres, LLP

[57] ABSTRACT

A vascular hemostasis device comprises a shaft coaxially received within a hollow tube, and having a distal end formed with an opposed pair of resilient grasping prongs. The tube has an open distal end that may be situated percutaneously adjacent a vascular puncture site. The shaft and the tube are axially movable with respect to one another, so that the distal end of the shaft may be selectively extended from and partially retracted into the distal end of the tube by means of an actuation member attached to the shaft. When the distal shaft end is in its extended position, the prongs are exposed from the distal end of the tube, and they resiliently expand to an open position. When the distal shaft end is moved to its retracted position, the prongs are partially retracted into the distal end of the tube, radially contracting them to a closed position. In contracting, the prongs grasp and gather tissue adjacent the puncture site to obstruct bleeding therefrom. In a first embodiment, the prongs are on a distal end portion, of resorbable material, that is detachable from the body of the shaft. The tube is a sleeve through which the shaft is slidably disposed, the sleeve being axially received within a trocar that is installed percutaneously to the puncture site. A second preferred embodiment includes a unitary shaft with the prongs at the distal end. The tube in which the shaft is axially disposed is the trocar itself.

21 Claims, 5 Drawing Sheets

PERCUTANEOUS HEMOSTASIS DEVICE

BACKGROUND OF THE INVENTION

This invention relates to the field of hemostasis devices; that is, medical instruments designed to stanch the flow of blood from a ruptured or punctured blood vessel. More specifically, in one aspect, the present invention relates to a percutaneous hemostasis device, i.e., a device that can reach through the skin and subcutaneous tissue to promote hemostasis in a perforated or punctured bodily lumen, such as a blood vessel. In another aspect, the present invention relates to the method of using such a device to promote hemostasis at a perforation or puncture site in a subcutaneous bodily lumen, particularly a blood vessel.

A growing number of therapeutic and diagnostic medical procedures involve the percutaneous introduction of instrumentation into a vein or artery. For example, percutaneous transluminal coronary angioplasty (PTCA), most often involving the femoral artery, is performed hundreds of thousands of times annually, while other vessel-piercing procedures (e.g., percutaneous coronary angiography and atherectomy) number more than two million per year.

In each event, the closing and subsequent healing of the resultant vascular puncture is critical to the successful completion of the procedure. Traditionally, the application of external pressure to the skin entry site has been employed to stem bleeding from the wound until clotting and tissue rebuilding have sealed the perforation. (See, for example, U.S. Pat. No. 5,342,388—Toller, which discloses an external pressure application device for effecting hemostasis in a femoral artery puncture.) In some situations, this pressure must be maintained for up to an hour or more, during which the patient is immobilized, often with sandbags or the like. With externally-applied manual pressure, both patient comfort and practitioner efficiency are impaired. Additionally, a risk of hematoma exists, since bleeding from the vessel may continue until sufficient clotting effects hemostasis. Also, external pressure application devices may be unsuitable for patients with substantial amounts of subcutaneous adipose tissue, since the skin surface may be a considerable distance from the vascular puncture site, thereby rendering skin compression inaccurate and thus less effective.

Consequently, devices have been developed for promoting hemostasis directly at the site of the vascular perforation. For example, there are devices that deploy intraluminal plugs within the vessel to close the puncture site, as disclosed in the following U.S. Pat. Nos.: 4,852,568—Kensey; 4,890,612—Kensey; 5,021,059—Kensey et al.; and 5,061,274—Kensey. Another approach is to deliver a tissue adhesive or clotting agent to the perforation site, as disclosed in the following U.S. Pat. Nos.: 5,221,259—Weldon et al.; 5,383,899—Hammerslag; 5,419,765—Weldon et al.; and 5,486,195—Myers et al. This method may entail some risk of disadvantageously introducing some of the adhesive or clotting agent into the bloodstream. Still another approach is the application of pressure directly to the perforation site, as exemplified by PCT International Publication Number WO 95/32671; U.S. Pat. No. 4,619,261—Guerrieo; and U.S. Pat. No. 4,929,246—Sinofsky, the last-named disclosing the simultaneous application of direct pressure to the perforated vessel and the direction of laser energy through an optical fiber to cauterize the wound. Yet another approach is disclosed in U.S. Pat. No. 5,275,616—Fowler, wherein a cylindrical plug is inserted along the shaft of a catheter segment extending from the skin surface to the blood vessel. The catheter is then removed so that the plug can expand as fluid is drawn into the plug from the vessel and the surrounding tissue. Unless pressure is applied, however, bleeding may occur around the plug into the subcutaneous tissue. A similar concept is disclosed in U.S. Pat. No. 5,391,183—Janzen et al., which discloses a variety of plug delivery devices, including threaded plug pushers and multilegged channels, that install a plug that may be resorbable.

Many of the above-noted devices rely, to varying degrees, on tactile sensation alone to indicate to the surgeon the proper placement of the puncture closing instrumentation, and they may also require upstream clamping of the blood vessel to reduce intraluminal pressure to approximately atmospheric pressure at the puncture site.

Another type of percutaneous vascular hemostasis device is exemplified in U.S. Pat. Nos. 5,417,699 and 5,527,322, both to Klein et al. This type of device comprises a mechanism for delivering a suture percutaneously to a vascular suturing site, and then tying the suture in situ. While such devices, if properly employed, are capable of very effectively stemming blood flow, they may require a relatively high degree of dexterity to be operated properly. Furthermore, they tend to be somewhat complex and expensive to manufacture, and thus are not practically employed as single use, disposable products. Consequently, sterilization is required between uses to reduce the risk of infection, thereby increasing their cost and inconvenience.

Accordingly, there has been a long-felt need for an effective percutaneous vascular hemostasis device that is relatively simple and inexpensive to manufacture and easy to use, that is adapted for use as disposable device, and that does not require the introduction of a foreign substance—such as a plug, tissue adhesive, or clotting agent—into the bloodstream.

SUMMARY OF THE INVENTION

Broadly, the present invention is a percutaneous vascular hemostasis device, comprising a hollow shaft having a distal end formed with at least one opposed pair of resilient grasping prongs. The interior of the shaft is dimensioned to accommodate a guide wire, while the shaft is externally dimensioned to be received within a coaxial hollow tube. The shaft and the tube are axially movable with respect to one another, so that the distal end of the shaft may be selectively extended from and partially retracted into the distal end of the tube. The shaft has a proximal end attached to an actuation member that is movable from a first position to a second position to move the shaft from its extended position to its partially retracted position. When the distal end of the shaft is in its extended position, the prongs are exposed from the distal end of the tube, whereby their resilience causes them to expand radially to an open position. When the actuation member is moved to its second position, the prongs at the distal end of the shaft are partially retracted into the distal end of the tube, radially contracting them to a closed position.

In a first preferred embodiment, the prongs are formed as a part of a distal end portion that is detachable from the body of the shaft. The detachable distal end portion is made of a resorbable material, of a type well known in the surgical arts. The tube is a sleeve through which the shaft is slidably disposed, the sleeve being dimensioned to be received within an introducer sheath or trocar, of the type that is typically used to provide percutaneous vascular access for surgical instruments. The mechanism for attaching the distal end portion of the shaft to the body of the shaft includes a pair of complementary coupling elements that are maintained in engagement by their containment within the sleeve. The distal end portion of the shaft is provided with an axially-slidable annular locking collar, likewise formed of the resorbable material.

The first preferred embodiment is used at the end of a percutaneous surgical procedure that has resulted in a perforation or puncture site in a bodily lumen, particularly a blood vessel. In the procedure, the trocar (sheath) and the guide wire have been deployed and then left in the surgical site, the distal end of the trocar being within the perforation or puncture site. The guide wire is threaded through the hollow shaft as the shaft and its surrounding sleeve are advanced distally down the length of the trocar, with the prongs just inside the distal end of the trocar, and with the actuation member in its first position. When the shaft and the sleeve are properly located with respect to the perforation or puncture site (i.e., in the adipose tissue external to the blood vessel and adjacent to the site), the trocar is retracted (moved proximally away from the site) to expose the prongs, which then expand radially. The actuation member is then moved to its second position to partially retract the distal end of the shaft into the distal end of the sleeve, whereby the prongs are radially contracted to their closed position and thereby grasp the tissue surrounding the perforation or puncture site. This grasping action causes the tissue to gather together in a way that occludes blood flow from the perforation or puncture site.

The retraction of the distal shaft end in the proximal direction causes the distal end of the sleeve to engage against the locking collar, pushing the collar distally part way over the prongs to lock them in their contracted, closed position. The guide wire is then withdrawn from the surgical site through the shaft of the hemostasis device, and the actuation member is moved distally, past its first position, to a third position, which in turn moves the shaft to an extreme distal position in which the coupling elements are removed from the sleeve. Removed from the constraints of the sleeve, the coupling elements disengage, thereby allowing the distal end portion of the shaft to be detached when the body of the shaft is withdrawn through the trocar. The detached end portion remains in place, the prongs locked closed by the locking collar, until it is resorbed, by which time the wound has sufficiently healed to avoid further bleeding.

In a variation of this first preferred embodiment, the prongs may be dimensioned and configured to be inserted into the lumen or vessel through the perforation or puncture site, and positioned against the interior wall surface surrounding the wound. When the prongs are closed, they gather the tissue together around the wound to fully or partially close the wound, thereby stemming the bleeding.

A second preferred embodiment includes a one-piece, unitary shaft with the prongs formed at the distal end. The tube in which the shaft is axially disposed is the trocar itself. This embodiment is located adjacent the wound in a manner similar to that of the first embodiment, with the actuation member in its first position, but with the distal end of the shaft, including the prongs, still enclosed within the trocar. The trocar is then withdrawn proximally, exposing the prongs so that they open to their expanded position. The actuation member is then moved to its second position to retract the distal end of the shaft partially into the distal end of the trocar, thereby causing the prongs to contract to their closed position. As in the first embodiment, the closing of the prongs results in tissue adjacent the wound being grasped and gathered together, thereby stemming the bleeding. The hemostasis device is left in place, with the prongs closed, until a sufficient degree of hemostasis is achieved to warrant removal of the device.

As will be better appreciated from the detailed description that follows, the present invention provides a reliable and easily used mechanism for promoting and achieving percutaneous vascular hemostasis. Moreover, hemostasis devices constructed in accordance with the present invention are relatively simple and inexpensive to manufacture, thereby lending themselves to single use, disposable products that reduce the risk of infection. Furthermore, the present invention may be made in such a way that its use does not expose the blood stream to a foreign substance, such as a plug or a coagulation accelerant or a tissue adhesive. On the other hand, the present invention may also be readily adapted for use in conjunction with electro-cauterization or laser cauterization, or with agents such as tissue adhesives and coagulation accelerants, if desired.

DETAILED DESCRIPTION OF THE INVENTION

Figure 1:
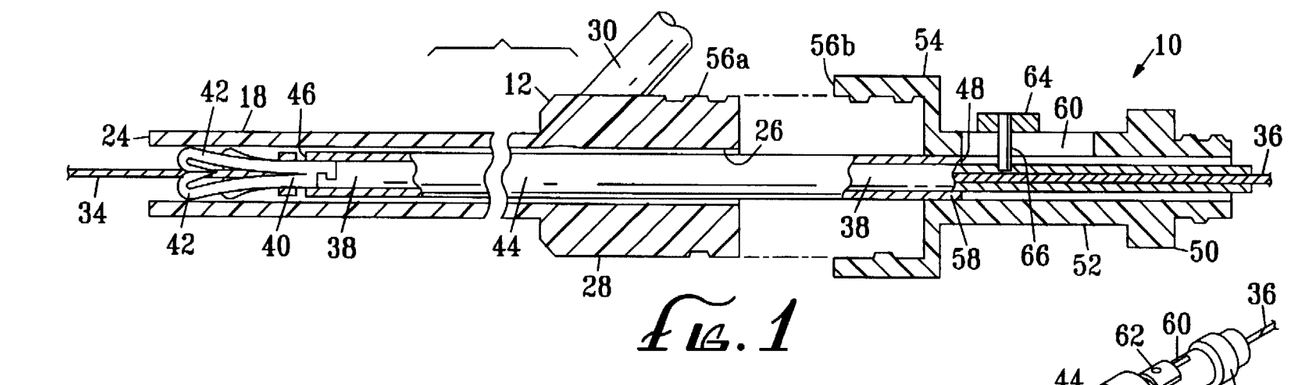
FIG. 1 is a longitudinal cross-sectional view of a percutaneous vascular hemostasis device, in accordance with a first preferred embodiment of the present invention, showing the device disposed within a surgical trocar prior to deployment of the device at a subcutaneous vascular perforation or puncture site.
Figure 2:
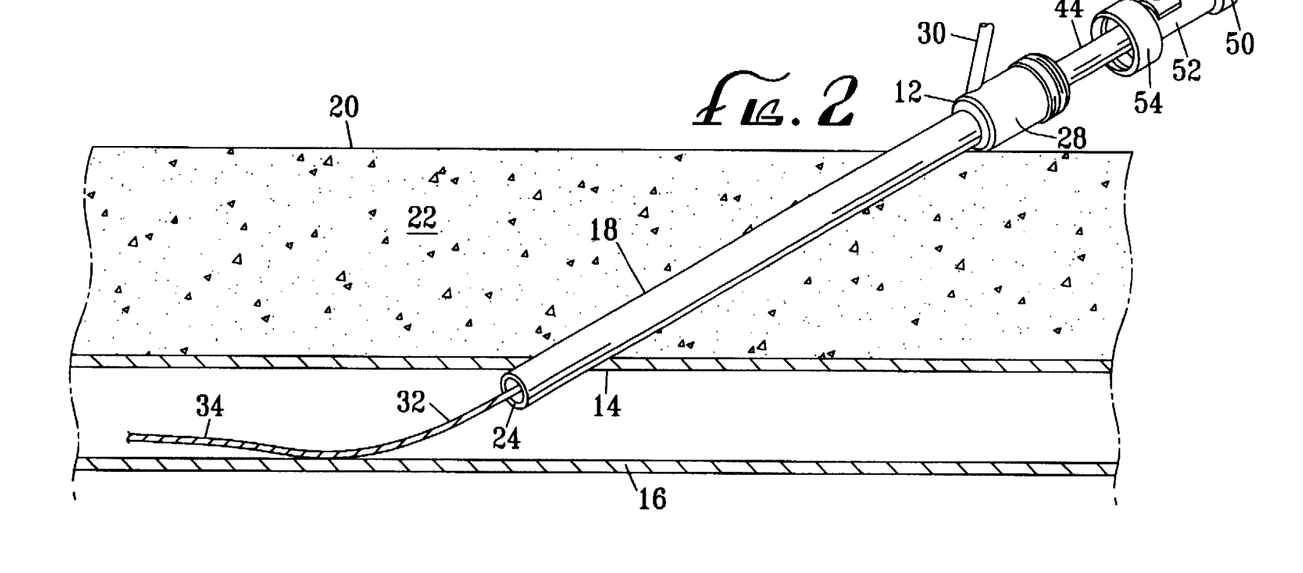
FIG. 2 is a perspective view of the device of FIG. 1, with the device disposed within a trocar prior to deployment at the vascular site, which is shown in cross-section.

Referring first to FIGS. 1 and 2, a percutaneous vascular hemostasis device 10, in accordance with a first preferred embodiment of the present invention, is shown disposed within a surgical sheath or trocar 12 prior to deployment of the device 10 at a perforation or puncture site 14 in a subcutaneous bodily lumen 16. For the purposes of the ensuing discussion, the lumen 16 will be referred below to as a blood vessel, although the adaptation of the present invention for use in procedures involving other organs will readily suggest itself to those skilled in the pertinent arts.

The trocar 12 is of a conventional type, commonly used in the above-mentioned surgical procedures, and, as shown in FIG. 2, it is positioned as it would be after the completion of such a surgical procedure. Specifically, the trocar 12 comprises an elongate hollow tube or barrel 18 that is inserted through the skin 20 and subcutaneous tissue 22, with an open internal or distal end 24 that has been inserted into the vessel 16 through the puncture site 14. The barrel 18 has an open external or proximal end 26 that extends from a surgical entry site in the skin 20, and that is formed into an enlarged-diameter fitting 28. The fitting 28 includes a port 30 that communicates with the interior of the trocar barrel 18, and that serves as a conduit for the introduction of a contrasting dye, of the type commonly used in many of the aforementioned surgical procedures.

As shown in FIG. 2, after the completion of the surgical procedure, a guide wire 32, used to guide surgical instruments down the trocar 12, has been left in place, threaded through the barrel 18, with a first or internal end 34 extending through the distal end 24 of the barrel 18 so as to be disposed within the vessel 16, and a second or external end 36 that extends out of the proximal end 26 of the barrel 18.

The hemostasis device 10 comprises an elongate, hollow, tubular shaft 38 having a main body portion and a distal end portion 40 that terminates in at least two, and preferably four, resilient prongs 42, as will be described in detail below. The inside diameter of the shaft 38 is large enough to allow the guide wire 32 to be freely threaded through it. The shaft 38 is slidably disposed within a coaxial sleeve 44, the outside diameter of which is slightly less than the inside diameter of the trocar barrel 18, so that there is a coaxial clearance space between the sleeve 44 and the barrel 18. The sleeve 44 has an open distal end 46 through which the distal end portion 40 of the shaft 38 extends, and an open proximal end 48, to which is attached a handle assembly 50.

The handle assembly 50 includes a hollow, tubular central portion 52 and a distal end portion formed as a cup-like hub 54, sized to mate with the trocar fitting 28. The hub 54 is removably attachable to the fitting 28, either by a friction fit, or by the use of mating threads 56a, 56b, as shown. The hub 54 has a central bore 58 that receives the proximal end 48 of the sleeve 44, and that communicates with the interior of the central portion 52. The shaft 38 has a proximal end portion that extends proximally from the proximal end 48 of the sleeve 44 and through the interior of the central portion 52 of the handle assembly, as best shown in FIG. 1.

The central portion 52 of the handle assembly 50 has an axial slot 60 that communicates with its interior. An actuation member 62 is slidable along the slot 60, and includes a thumb button 64 attached to one end of a stem 66 that rides in the slot 60. The other end of the stem is fixed to the proximal end portion of the shaft 38. Movement of the actuation member 62 in the slot 60 thus causes the shaft 38 to move axially within and with respect to the sleeve 44, as explained below.

Figure 8:
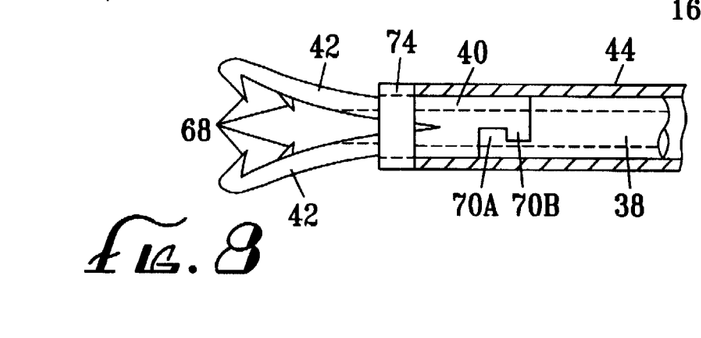
FIG. 8 is a detailed elevational view of the distal end portion of the embodiment of FIGS. 1 through 7, showing the prongs in their open position.

As best shown in FIGS. 1 and 8, the distal end portion 40 of the shaft terminates, in the preferred embodiment, in two opposed pairs of prongs 42. The prongs 42 have a naturally "open" position in which they diverge radially outwardly at an angle that is preferably about 30° (although this parameter is not critical), and their natural resilience causes them to return to this naturally open position if they are squeezed together (i.e., radially inwardly). In the open position, as shown, for example, in FIG. 8, the ends of the prongs 42 are preferably about 6 mm apart. In the preferred (four prong) embodiment, one of each opposed pair of the prongs 42 is somewhat longer than the other of the pair, for purposes that will be explained below. In a two-prong embodiment, there would be a single opposed pair of prongs, one of which would similarly be somewhat longer than the other.

Figure 10:
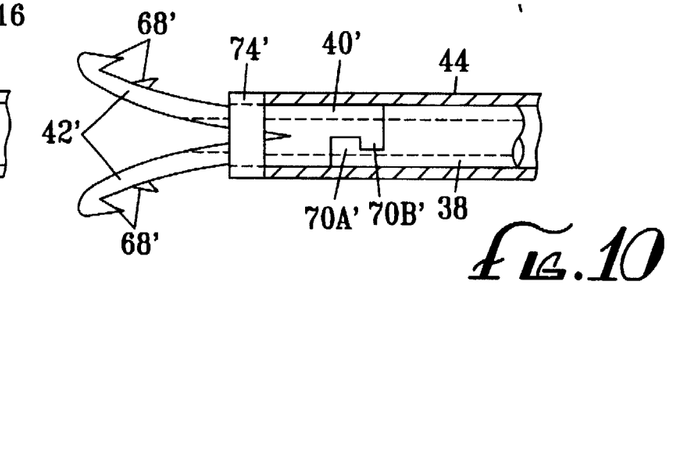
FIG. 10 is a view similar to that of FIG. 8, but showing a variant of the of the prong configuration.

As shown in FIGS. 1 and 8, each of the prongs 42 terminates in an inwardly-turned hook or barb 68. FIG. 10 illustrates a variant distal end portion 40', having four resilient prongs 42', each of which terminates in an outwardly-turned barb 68'. The purpose of the barbs 68, 68' will be explained below.

As best shown in FIGS. 8 and 10, the distal end portion 40, 40' is detachably connected to the main body portion of the shaft 38. The preferred mechanism for effecting this detachable connection is a first coupling knuckle 70a (70a' in FIG. 10) at the distal end of the body of the shaft 38, and a complementary second coupling knuckle 70b (70b' in FIG. 10) at the proximal end of the distal end portion 40, 40'. The first and second coupling knuckles are maintained in co-engagement by their containment within the sleeve 44. When the joint formed by the coupling knuckles 70a, 70b (70a', 70b') is removed from within the sleeve 44, as described below, they disengage with, at most, a slight twisting or jiggling of the shaft 38.

As is also shown most clearly in FIGS. 8 and 10, the distal end portion 40, 40' is provided with a slidable annular locking collar 74 (74' in FIG. 10). The locking collar 74, 74' can be pushed distally over the prongs 42, 42' by the distal end of the sleeve 44, as will be described below, to lock the prongs 42, 42' in their closed position.

As will be made clear from the explanation of the operation of the device 10, as set forth below, the distal end portion 40, 40' (including the prongs 42, 42' and the locking collar 74, 74') advantageously should be made of a bioresorbable material, of a type that is well known in the medical arts. A number of such materials will exhibit the requisite degree of resilience to provide the self-opening prong function described above.

The method of using the hemostasis device 10 is illustrated in FIGS. 2 through 9. As mentioned above, the device 10 is used with a trocar 12 and a guide wire 32 that have been left in place after the completion of a surgical procedure that has created or exploited a puncture site 14 in a blood vessel 16. At this time, the distal end 24 of the trocar barrel 18 is disposed within the puncture site 14. The external end 36 of the guide wire 32 is passed through the interior of the shaft 38 until it extends out of the proximal end of the handle assembly 50, as shown in FIG. 2. With the actuation member 62 in a first ("intermediate") position, the distal end portion 40 of the shaft 38 is exposed from the distal end 46 of the sleeve 44, but the joint formed by the coupling knuckles 70a, 70b is still contained within the sleeve 44. The distal end portion 40 of the shaft 38 and the distal end 46 of the sleeve 44 are inserted into the proximal end 26 of the barrel 18 of the trocar 12. This action causes the prongs 42 to contract to their closed position. The device 10 is then pushed part way down the trocar 12 until the prongs 42 reside just proximally from the distal end 24 of the trocar barrel 18, as best shown in FIG. 1. At this point in the deployment process, the hub 54 of the handle portion 50 is spaced from the proximal fitting 28 of the trocar 12.

Figure 3:
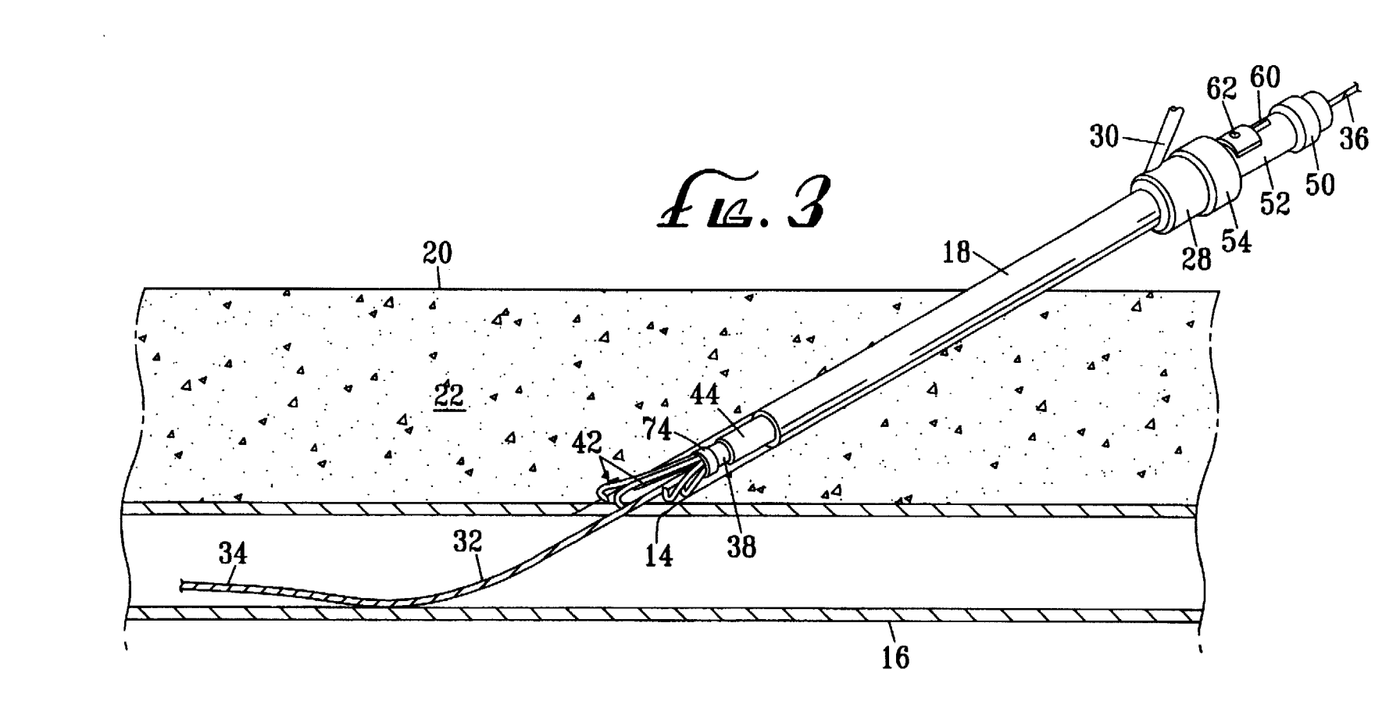
FIG. 3 is a view similar to that of FIG. 2, showing the device and the trocar positioned for deployment of the device at the vascular site, with the prongs of the device in their open position.
Figure 4:
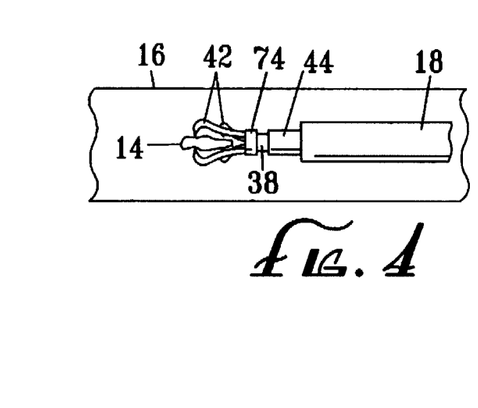
FIG. 4 is a top plan view of the distal portions of the device and trocar, positioned for deployment at the vascular site as in FIG. 3, with the prongs open.

Next, the trocar 12 and the hemostasis device 10 are withdrawn together proximally from the puncture site 14 until the distal end 24 of the trocar barrel 18 is located in the subcutaneous tissue 22 surrounding the vessel 16, just a few millimeters above it. This position may be confirmed fluoroscopically, either by marking the distal end 24 of the trocar barrel 18 with a fluorescent marker (not shown), or by introducing a contrasting dye into the barrel 18 and out the distal end 24 via the port 30. The proper orientation of the prongs 42 may also be visualized by the use of a marker (not shown), to assure that the longer prongs extend toward the far side of the puncture site 14 and the shorter prongs extend toward the near side of the puncture site 14 when the trocar 12 is oriented at an angle with respect to the puncture site 14, as shown. The trocar 12 is then withdrawn proximally with respect to the sleeve 44 of the device 10, as shown in FIG. 3, to expose the prongs 42. The proximal fitting 28 of the trocar 12 is advantageously coupled, at this point in the procedure, to the hub 54 of the handle portion 50 of the device 10. At this point in the procedure, the prongs 42 are in their radially-expanded, open position, as shown in FIGS. 3 and 4.

Figure 5:
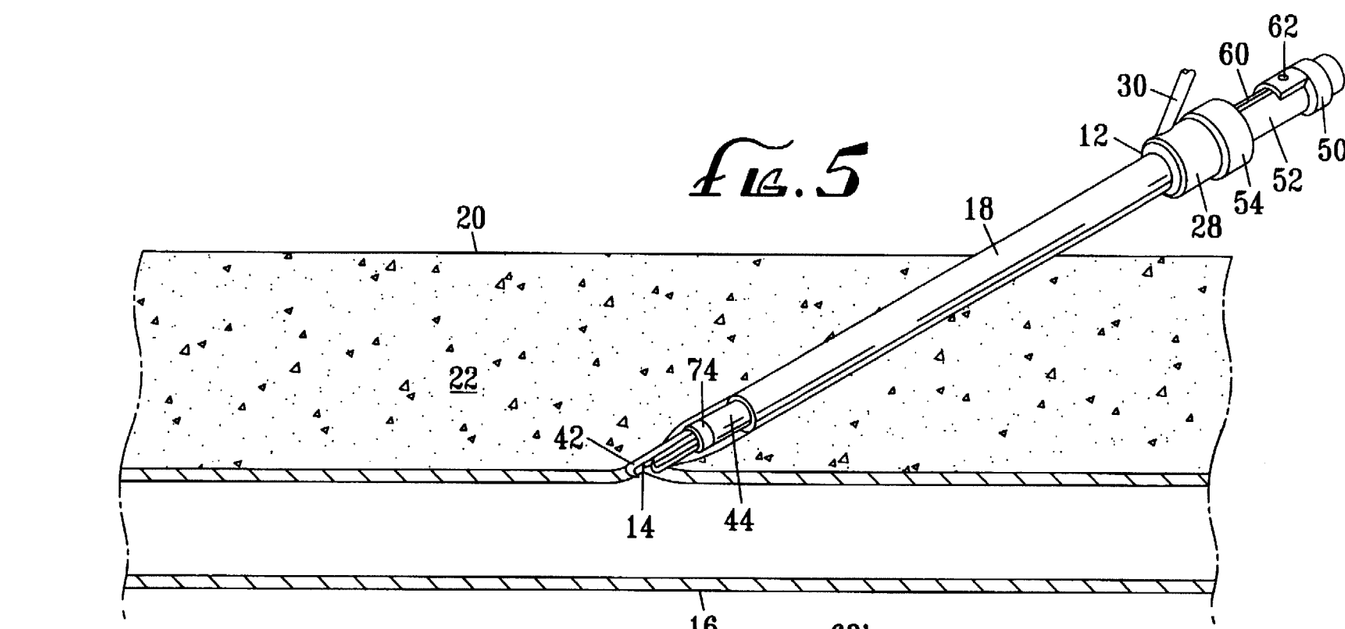
FIG. 5 is a view similar to that of FIG. 3, but with the prongs of the device in their closed position.
Figure 6:
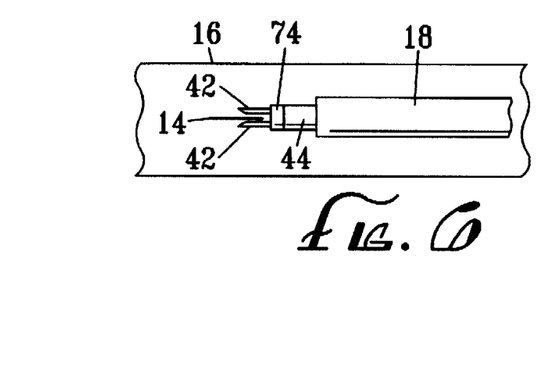
FIG. 6 is a top plan view of the distal portions of the device and trocar, positioned for deployment at the vascular site as in FIG. 5, with the prongs closed.

Next, the actuation member 62 is moved proximally to its second ("proximal") position. This action moves the shaft 38 axially with respect to the sleeve 44 in the proximal direction, whereby the distal end portion 40 of the shaft 38 is partially retracted into the sleeve 44, thereby radially contracting the prongs 42 to their closed position as they retract into the sleeve 44. As the prongs 42 close toward each other, the barbs 68 at the ends of the prongs 42 grasp the surrounding tissue and/or the vessel wall tissue, and gather it together adjacent the puncture site 14, thereby creating an obstruction to the flow of blood from the site 14, as shown in FIGS. 5 and 6. It may be advantageous, just prior to or simultaneously with this shaft actuation step, to provide a slight downward pressure (i.e., in the distal direction) on the entire assembly (the device 10 and the trocar 12) to assure a better grasp of tissue by the prongs 42.

Figures 7, 9:
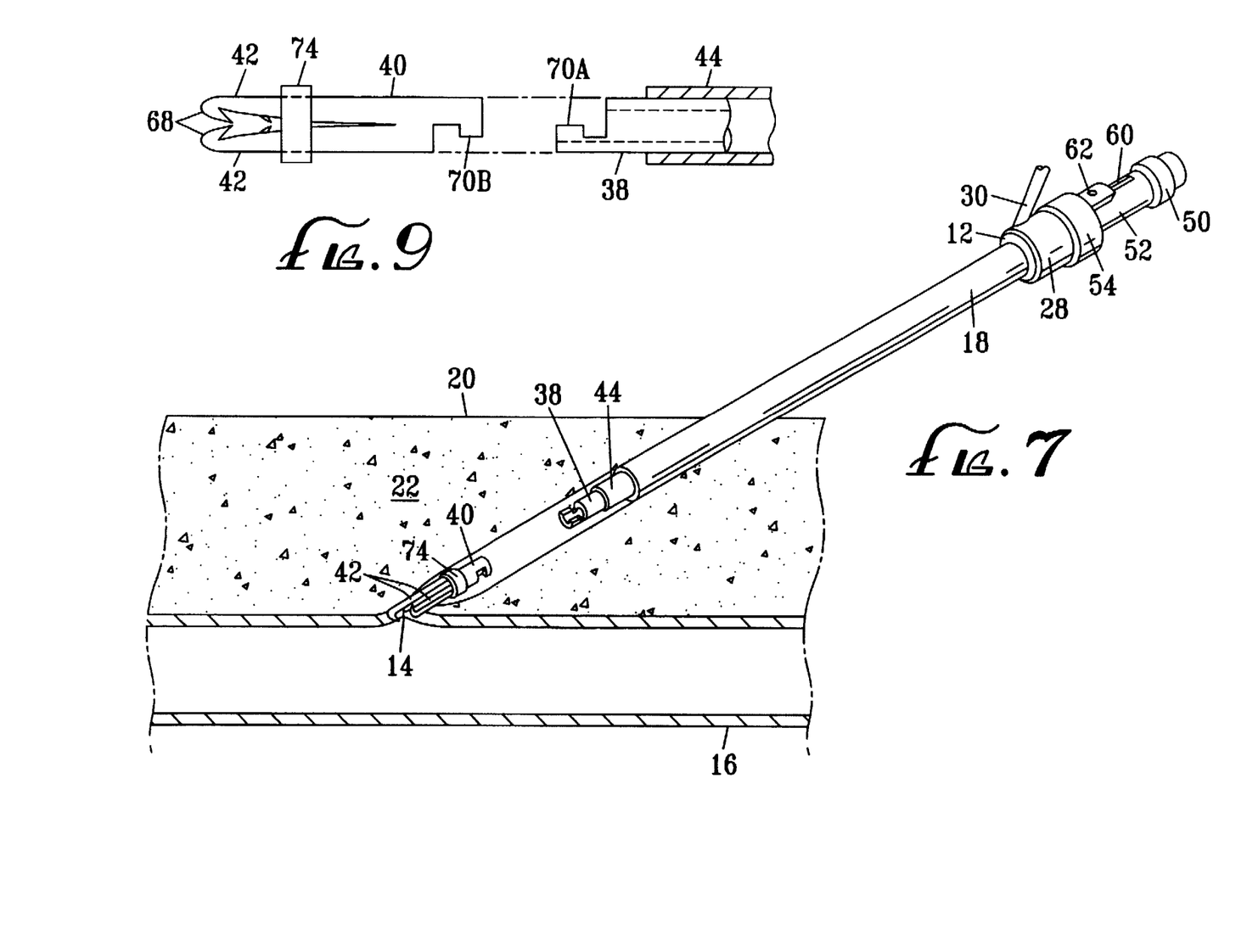
FIG. 7 is a view similar to that of FIG. 5, showing the separation of the distal end portion of the device after it has been deployed at the vascular site.
FIG. 9 is a view similar to that of FIG. 8, but showing the prongs in their closed position.

The retraction of the distal end portion 40 of the shaft 38 into the sleeve 44 brings the locking collar 74 into engagement against the distal end 46 of the sleeve 44, thereby forcing the collar 74 distally part way over the prongs 42 to lock them in their contracted, closed position. The guide wire 32 is then withdrawn from the surgical site through the shaft 38 of the hemostasis device 10, and the actuation member 62 is moved distally, past its first position, to a third ("distal") position, which in turn moves the shaft 38 to an extreme distal position in which the joint formed by the coupling knuckles 70a, 70b is removed from the sleeve 44, as shown in FIG. 9. Removed from the constraints of the sleeve 44, the coupling knuckles 70a, 70b disengage, thereby allowing the distal end portion 40 of the shaft 38 to be detached when the body of the shaft 38 is withdrawn through the trocar 12. The detached end portion 40 remains in place, the prongs 42 locked closed by the locking collar 74, until it is resorbed, by which time the puncture site 14 has sufficiently healed to avoid further bleeding.

Referring again to FIGS. 8 and 10, it is seen that the inwardly-directed barbs 68 of the prongs 42 shown in FIG. 8 are adapted particularly for grabbing tissue at or closely adjacent to the exterior wall surface of the vessel 16 without entering into the puncture site 14. On the other hand, the outwardly-directed barbs 68' of the variant prongs 42' of FIG. 10 are better adapted for entering the puncture site 14, and then grabbing and gathering together the tissue of the vessel wall from inside the vessel 16. This configuration thus makes removal of the shaft distal end portion 40' and the prongs 42' impractical; therefore, the hook configuration of FIG. 10 necessitates the use of a shaft distal end portion that is detachable.

Figure 11:
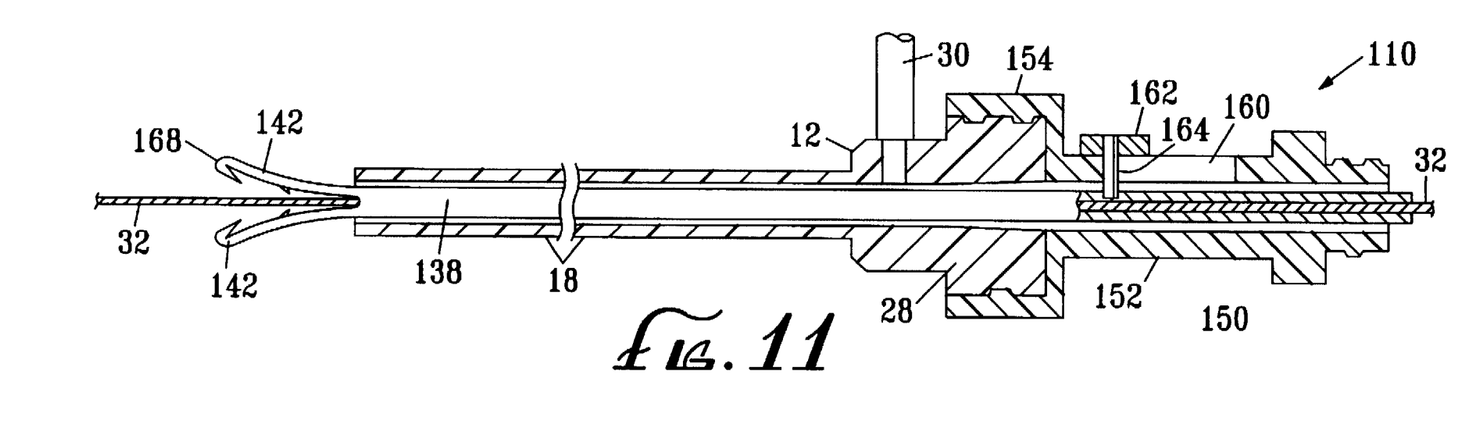
FIG. 11 is a longitudinal cross-sectional view of a percutaneous vascular hemostasis device in accordance with a second preferred embodiment of the invention, as disposed within a surgical trocar, and with the prongs in their open position.
Figure 12:
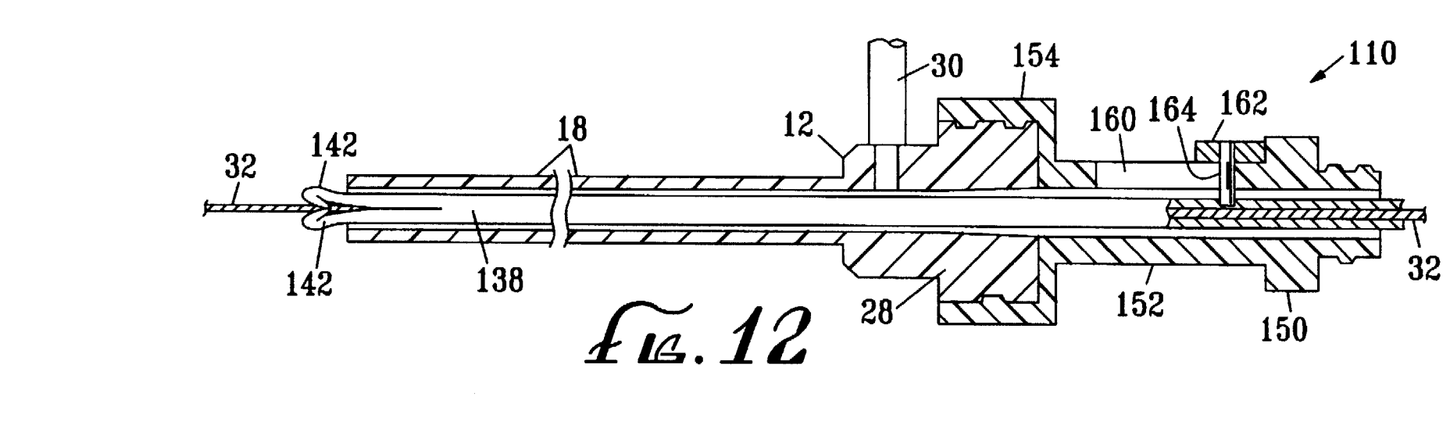
FIG. 12 is a view similar to that of FIG. 11, but showing the prongs in their closed position.

FIGS. 11 and 12 illustrate a hemostasis device 110, in accordance with a second preferred embodiment of the invention. This embodiment includes a one-piece, unitary, hollow shaft 138 with a plurality of prongs 142 at its distal end. In this embodiment there would not need to be a sleeve between the shaft 138 and the trocar barrel 18; rather, the shaft 138 may be installed directly into the trocar barrel.

More specifically, this embodiment includes a handle portion 150 having a hollow, tubular central portion 152 joined to a cup-like distal hub 154 that is removably attachable to the proximal fitting 28 of the trocar 12, as described above. The central portion includes an axial slot 160, and an actuation member 162 is slidably disposed within the slot 160, with a stem 164 that is attached to the shaft 138 through the slot 160. The actuation member 162 is movable between a first ("distal") position and a second ("proximal") position, whereby the shaft 138 is moved axially with respect to the coaxial trocar barrel 18 between an extended position and a retracted position, respectively. The distal end of the shaft 138 is formed into one or more opposed pairs of resilient prongs 142 (preferably two pairs), configured with inwardly-turned barbs 168. As in the first embodiment, one prong of each opposed pair of prongs 142 is preferably longer than the other prong in the pair.

As with the above-described first embodiment, use of the hemostasis device 110 of the second embodiment begins after the trocar 12 and the guide wire 32 have been left in place upon completion of a surgical procedure that has created or exploited a puncture site 14 in a blood vessel 16. At this time, the distal end 24 of the trocar barrel 18 is disposed within the puncture site 14. The external end 36 of the guide wire 32 is passed through the interior of the shaft 138 until it extends out of the proximal end of the handle assembly 150. With the actuation member 162 in its distal position, the distal end of the shaft 138, including the prongs 142, is inserted into the proximal end 26 of the barrel 18 of the trocar 12. This action causes the prongs 142 to contract to their closed position. The device 110 is then pushed part way down the trocar 12 until the prongs 142 reside just proximally from the distal end 24 of the trocar barrel 18. At this point in the deployment process, the hub 154 of the handle portion 150 is spaced from the proximal fitting 28 of the trocar 12, such as is shown in FIG. 2, with the prongs 142 still enclosed by the trocar 12, just proximally from its distal end 24.

The trocar 12 and the device are withdrawn together proximally from the puncture site 14 until the distal end 24 of the trocar barrel 18 is located in the subcutaneous tissue 22 surrounding the vessel 16, just a few millimeters above it. This position, as well as the proper orientation of the prongs 142, may be visualized and confirmed by means similar to those described above in connection with the first embodiment. As shown in FIG. 11, the trocar 12 is then withdrawn proximally with respect to the shaft 138, exposing the prongs 142 so that they open to their expanded position, and the proximal fitting 28 of the trocar 12 is secured to the hub 154 of the handle portion 150 to lock the trocar 12 and the hemostasis device 110 together. The actuation member 162 is then moved to its proximal position to retract the prongs 142 partially into the distal end 24 of the trocar, thereby causing the prongs 142 to contract to their closed position, as shown in FIG. 12. As in the first embodiment, the closing of the prongs results 142 in tissue adjacent the puncture site 14 being grasped and gathered together, thereby stemming the bleeding. Also, as in the first embodiment, the retraction of the prongs 142 may be accompanied or immediately preceded by a slight downward pressure on the entire assembly, to enhance the grasping action of the prongs. The hemostasis device 110 is left in place, with the guide wire 32 either having been removed or also left in place, with the prongs 142 closed, until a sufficient degree of hemostasis is achieved to warrant removal of the device.

When it is desired to remove the device 110, the actuation member 162 is moved to its distal position to expose the prongs 142, thereby allowing them to expand resiliently and thus release their grip on the tissue. The hub 154 of the device 110 is then decoupled from the proximal fitting 28 of the trocar 12, and the device 110 is withdrawn from the trocar.

It will be appreciated from the foregoing that the present invention provides a reliable and easily used mechanism for promoting and achieving percutaneous vascular hemostasis. Moreover, hemostasis devices constructed in accordance with the present invention are relatively simple and inexpensive to manufacture, thereby lending themselves to single use, disposable products that reduce the risk of infection. Furthermore, the present invention may be made in such a way that its use does not expose the blood stream to a foreign substance, such as a plug or a coagulation accelerant or a tissue adhesive. Still another advantage is that the present invention can readily be adapted to the closure of wounds in a variety of subcutaneous bodily lumens, other than blood vessels.

It will also be appreciated that the present invention may be adapted for use with other hemostasis-promoting mechanisms. For example, a tissue adhesive or coagulation accelerant may, if desired, be introduced to the puncture or perforation site through the port 30, or through the interior of the shaft. With the second (unitary shaft) embodiment, electrocauterization can be implemented by using a conductive metal shaft that is connected to an electrocautery generator, of a type well-known in the surgical arts. (The electrocautery shaft and tip would preferably be coated with an insulating material so that only the desired area delivers coagulating energy.) Still another mechanism may be an optical fiber disposed axially through the interior of the shaft, or through the trocar along side the shaft. The fiber would carry laser energy to the puncture or perforation site to promote hemostasis.

While two preferred embodiments have been described herein, it will be appreciated that a number of modifications and variations will suggest themselves to those skilled in the pertinent arts. For example, the number and configuration of the prongs and their barbs may be a altered to suit differing surgical needs and applications. Likewise, with respect to the first embodiment, there may be any number of suitable equivalents to the specific means disclosed herein for removably attaching the distal shaft end portion to the body of the shaft. These and other modifications and variations that may suggest themselves should be considered within the spirit and scope of the present invention, as defined in the claims that follow.

What is claimed is:

1. A percutaneous vascular hemostasis device, comprising:

an elongate hollow tube having an open distal end;

an elongate shaft disposed coaxially within the tube and having a proximal end portion and a distal end portion, the distal end portion terminating in at least one pair of resilient prongs, each of the prongs having an inwardly-turned end, whereby the shaft and the tube are axially movable with respect to one another, so that the distal end portion of the shaft may be selectively extended from and partially retracted into the distal end of the tube; and an actuation member attached to the proximal end portion of the shaft, the actuation member being movable from a first position to a second position respectively to move the shaft from an extended position in which the distal end portion of the shaft extends from the distal end of the tube, to a retracted position in which the distal end portion of the shaft is at least partially retracted into the distal end of the tube;

whereby, when the shaft is in its extended position, the prongs are exposed from the distal end of the tube, whereby their resilience causes them to expand radially to an open position, and when the shaft is in its retracted position, the prongs are partially retracted into the distal end of the tube, radially contracting them to a closed position.

2. The hemostasis device of claim 1, wherein the shaft includes a main body portion, and wherein the distal end portion of the shaft is detachable from the main body portion.

3. The hemostasis device of claim 2, wherein the distal end portion is formed of a bioresorbable material.

4. The hemostasis device of claims 1, 2, or 3, wherein the distal end portion terminates in two opposed pairs of resilient prongs, one of each pair being longer than the other of each pair.

5. The hemostasis device of claim 1 wherein the tube is a surgical trocar.

6. The hemostasis device of claim 5, wherein the distal end portion terminates in two opposed pairs of resilient prongs, one of each pair being longer than the other of each pair.

7. The hemostasis device of claims 1, 2, or 3, wherein the tube is a sleeve dimensioned to be coaxially received within a surgical trocar.

8. The hemostasis device of claims 1, 2, or 3, wherein the distal end portion of the shaft includes a locking mechanism that is movable on the shaft to lock the prongs in their closed position, without contacting the inwardly-turned ends of the prongs, when the shaft is moved to its retracted position.

9. The hemostasis device of claim 8, wherein the locking mechanism comprises an annular locking collar that is operatively engaged by the distal end of the tube when the shaft when the shaft is moved to its retracted position.

10. The hemostasis device of claim 2, wherein the tube is a sleeve dimensioned to be coaxially received within a surgical trocar, and wherein the shaft is axially movable to a third position relative to the sleeve, whereby the distal end portion is detachable from the main shaft body when the shaft is moved to the third position.

11. The hemostasis device of claim 10, wherein the distal end portion of the shaft includes a locking mechanism that is movable on the shaft to lock the prongs in their closed position, without contacting the inwardly-turned ends of the prongs, when the shaft is moved to its retracted position.

12. The hemostasis device of claim 11, wherein the sleeve has a distal end, and wherein the locking mechanism comprises an annular locking collar that is operatively engaged by the distal end of the sleeve when the shaft when the shaft is moved to its retracted position.

13. A percutaneous vascular hemostasis device, comprising:

an elongate, hollow sleeve having an open distal end and dimensioned to be axially received in a surgical trocar;

an elongate shaft disposed coaxially within the sleeve and comprising a proximal end portion, a main body portion, and a distal end portion that is detachably connected to the main body portion, the distal end portion terminating in at least one opposed pair of resilient prongs, each of the prongs having an inwardly-turned end, whereby the shaft and the sleeve are axially movable with respect to one another among first, second, and third positions; and an actuation member attached to the proximal end portion of the shaft, the actuation member being operable to move the shaft among the first, second, and third positions;

whereby in the first position the distal end portion of the shaft extends from the distal end of the sleeve, in the second position the distal end portion of the shaft is at least partially retracted into the distal end of the sleeve, and in the third position the distal end portion is detachable from the main body portion of the shaft;

whereby, when the shaft is in its first position, the prongs are exposed from the distal end of the sleeve, whereby their resilience causes them to expand radially to an open position, and when the shaft is in its second position, the prongs are partially retracted into the distal end of the sleeve, radially contracting them to a closed position.

14. The hemostasis device of claim 13, wherein the distal end portion is formed of a bioresorbable material.

15. The hemostasis device of claim 14, wherein the distal end portion terminates in two opposed pairs of resilient prongs, one of each pair being longer than the other of each pair.

16. The hemostasis device of claims 13, 14, or 15, wherein the distal end portion of the shaft includes a locking mechanism that is movable on the shaft to lock the prongs in their closed position without contacting the inwardly-turned ends of the prongs, when the shaft is moved to its second position.

17. The hemostasis device of claim 16, wherein the locking mechanism comprises an annular locking collar disposed on the distal end portion of the shaft, and operatively engaged by the distal end of the sleeve when the shaft is moved to its second position.

18. A method of promoting hemostasis at a perforation or puncture site in a subcutaneous lumen, comprising the steps of:

(1) providing percutaneous access to the site through a surgical trocar, the trocar having open distal and proximal ends, the distal end being disposed within the lumen through the site;

(2) providing an elongate shaft having a proximal end portion and a distal end portion, the distal end portion terminating in at least one opposed pair of resilient prongs, each of the prongs having an inwardly-turned end;

(3) installing the shaft axially into the trocar so that the prongs reside within the trocar near the distal end of the trocar;

(4) withdrawing the trocar and the shaft together a sufficient distance to place the distal end of the trocar external to the lumen and adjacent to the site;

(5) withdrawing the trocar proximally with respect to the shaft a sufficient distance to expose the prongs, whereby the prongs expand radially to an open position external to the lumen; and (6) moving the shaft proximally with respect to the trocar so as to retract the prongs partially into the distal end of the trocar, whereby the prongs are radially contracted to a closed position so as to grasp and gather together tissue adjacent the site external to the lumen, whereby the flow of blood from the site is substantially inhibited.

19. The method of claim 18, further comprising the step of:

(7) when hemostasis has been achieved, withdrawing the shaft from the trocar.

20. The method of claim 19, wherein the step of withdrawing the shaft from the trocar comprises the steps of:

(7)(a) moving the trocar proximally with respect to the shaft so as to expose the prongs, whereby the prongs expand radially to their open position; and (7)(b) pulling the shaft proximally through the trocar.

21. The method of claim 18, wherein the distal end portion of the shaft is detachable and formed of a bioresorbable material, and wherein the method further comprises the steps of:

(7) detaching the distal end portion of the shaft while the prongs are in their closed position and grasping the tissue; and (8) withdrawing the shaft from the trocar while leaving the detached distal end portion in place adjacent the site until it is resorbed.

* * * * *